US010105091B2

(12) United States Patent
Papay et al.

(10) Patent No.: US 10,105,091 B2
(45) Date of Patent: Oct. 23, 2018

(54) METHODS OF USING NERVE EVOKED POTENTIALS TO MONITOR A SURGICAL PROCEDURE (71) Applicants: THE CLEVELAND CLINIC FOUNDATION, Cleveland, OH (US); Autonomic Technologies, Inc., Redwood City, CA (US)

(72) Inventors: Francis A. Papay, Westlake, OH (US); Mike Hardage, Redwood City, CA (US); Anthony V. Caparso, San Francisco, CA (US); Benjamin D. Pless, Atherton, CA (US)

(73) Assignees: The Cleveland Clinic Foundation, Cleveland, OH (US); Autonomic Technologies, Inc., Redwood City, CA (US)

( * ) Notice: Subject to any disclaimer, the term of this patent is extended or adjusted under 35 U.S.C. 154(b) by 193 days.

(21) Appl. No.: 14/205,784

(22) Filed: Mar. 12, 2014

(65) Prior Publication Data
US 2014/0276195 A1 Sep. 18, 2014

Related U.S. Application Data
(60) Provisional application No. 61/777,576, filed on Mar. 12, 2013.

(51) Int. Cl.
A61B 5/00 (2006.01)
A61B 5/04 (2006.01)
(Continued)

(52) U.S. Cl.
CPC ........ *A61B 5/4836* (2013.01); *A61B 5/04001* (2013.01); *A61B 5/0484* (2013.01); *A61B 5/4893* (2013.01); *A61N 1/08* (2013.01)

(58) Field of Classification Search
CPC . A61B 5/04001; A61B 5/0484; A61B 5/4836; A61B 5/0478; A61B 5/4893; A61N 1/08; A61N 1/36142; A61N 1/0551
See application file for complete search history.

(56) References Cited

U.S. PATENT DOCUMENTS 7,799,021 B2    9/2010  Leung et al.
8,412,336 B2 *  4/2013  Pless ............... A61B 1/00135
                                              607/115

(Continued)

OTHER PUBLICATIONS

Friedman et al., "Monitoring of Sensory Evoked Potentials is Highly Reliable and Helpful in the Operating Room", J Clin. Monit., Jan. 1987, 3(1), 38-44. Abstract.

(Continued)

Primary Examiner — Rene Towa
Assistant Examiner — H. Q. Nguyen
(74) Attorney, Agent, or Firm — Tarolli, Sundheim, Covell & Tummino LLP (57) ABSTRACT Methods for intra-operatively monitoring nerve evoked potentials such as somatosensory nerve evoked potentials during a surgical procedure. The methods include orthodromic and antidromic monitoring of nerve evoked potentials. Monitoring includes navigating the surgical pathway to avoid insult to anatomical tissue, minimizing activation of sensory nerves that result in undesirable side effects in a patient, and determining the suitable location for placement of an implantable medical device.

8 Claims, 4 Drawing Sheets (51) Int. Cl.
*A61B 5/0484* (2006.01)
*A61N 1/08* (2006.01)

(56) References Cited

U.S. PATENT DOCUMENTS

| | | | | |
|---|---|---|---|---|
| 2002/0055761 A1* | 5/2002 | Mann | ............... | A61N 1/36007 |
| | | | | 607/41 |
| 2006/0206163 A1* | 9/2006 | Wahlstrand | .......... | A61N 1/0502 |
| | | | | 607/46 |
| 2010/0286554 A1* | 11/2010 | Davis | ................ | A61B 5/04001 |
| | | | | 600/554 |
| 2014/0135589 A1* | 5/2014 | Osorio | ................ | A61N 1/0539 |
| | | | | 600/301 |

OTHER PUBLICATIONS

Gentili et al., "Montioring of Sensory Evoked Potentials During Surgery of Skull Base Tumours", The Canadian Journal of Neurological Sciences, 1985, 12: 336-340.

Shih et al., "Intraoperative Localization of Sensorimotor Cortex by Cortical Somatosensory Evoked Potentials", J Formos Med Assoc., Nov. 1991, 90(11): 1049-54. Abstract.

* cited by examiner

METHODS OF USING NERVE EVOKED POTENTIALS TO MONITOR A SURGICAL PROCEDURE

CROSS-REFERENCE TO RELATED APPLICATIONS

The present application claims priority to U.S. Provisional Application No. 61/777,576, filed on Mar. 12, 2013, which is incorporated by reference herein.

TECHNICAL FIELD

The present invention generally relates to intra-operative monitoring of nerve evoked potentials, including somatosensory nerve evoked potentials. More specifically, the present invention relates to using nerve evoked potentials to assist in navigating a surgical pathway during a surgical procedure.

BACKGROUND

Nerve evoked potentials are the electrical signals or responses generated by the nervous system, generally referred to as nerve action potentials, in response to stimuli. The electrical signals can be single event trials or averaged single event trials presented as an evoked response or an evoked potential. Nerve evoked potentials are considered neurophysiological representations of peripheral nerve, spinal cord, and brain function. Intra-operative neurophysiological (IONM) monitoring of such nerve evoked potentials is assessed for latency and amplitude measurements that reflect both sensory and motor nerve fiber function. Generally, such intra-operative nerve evoked potentials are well established for clinically evaluating the electrophysiological presentation in patients with neurological symptoms.

Evaluating function of the sensory nervous system during surgery has been performed since the late 1970s. Intra-operative somatosensory evoked potentials (SSEP) monitoring is used to assess the functional integrity of the sensory nervous system pathways during surgical operations that put the spinal cord or brain at risk for significant ischemic or traumatic injury. The operative team identifies the neurological region at risk and selects a sensory pathway that carries a physiological signal through that region.

Currently, placement of stimulating electrodes has been largely limited by either radiologic evidence of positioning and placement during surgery. Since most patients are under general anesthesia and unconscious, the patients cannot elicit any sensory perceptions and/or autonomic responses. As such, there is a need for observing a real time physiological response that is independent of a patient's consciousness or perceptions.

SUMMARY

The present invention relates to intra-operative neurophysiological monitoring of nerve evoked potentials during a surgical procedure. In an embodiment, the present invention provides a method of intra-operatively monitoring a surgical procedure performed on a patient by stimulating a stimulation site of the patient's body and recording electrical activity from a recording site of the patient's body. The method further comprises determining if the stimulation elicits a somatosensory nerve evoked potential in a nerve comprising sensory fibers that propagates in an antidromic direction and innerves the recording site. The surgical procedure is monitored based on this determination.

In another embodiment, the present invention provides a method of intra-operatively monitoring a surgical procedure involving dissection of a patient's body. The method includes stimulating a stimulation site of the patient's body within stimulation parameters and recording electrical signals from a recording site of the patient's body in response to the stimulation. The method further includes determining a baseline nerve evoked potential based on adjusting the stimulation parameters to obtain a stable latency and amplitude of the recorded electrical signals. The method further includes dissecting the tissue and determining a nerve evoked potential. The nerve evoked potential is compared to the baseline nerve evoked potential and any change to the latency and the amplitude of the nerve evoked potential is observed. The method further comprises dissecting the tissue further and determining another nerve evoked potential. This another nerve evoked potential is compared to the baseline nerve evoked potential and any change to the latency and amplitude of the another nerve evoked potential is observed. The method further includes continuing to dissect the tissue until dissection is complete. The surgical procedure is monitoring during the dissection.

DETAILED DESCRIPTION

The present invention relates to monitoring a surgical procedure intra-operatively using nerve evoked potentials. Although the disclosure below will be described mainly with respect to implanting a neurostimulator within the pterygopalatine fossa (PPF) of a patient, the methods can apply to other surgical procedures involving dissection where nerve evoked potentials can assist the surgeon in monitoring the surgical pathway to avoid unwanted stimulation of nerves, unintended damage to tissue along the surgical pathway, and/or determining the suitable implantation site for an implantable medical device. Other exemplary surgical procedures include skull-based surgery; maxillofacial surgery; paranasal sinus surgery; anterior and middle cranial fossa surgery; and ablative and reconstructive surgery of the head and neck.

As used herein, a "patient" refers to a mammal suffering from a medical condition and who is in need of treatment. Preferably, the patient is a human being. The disclosure refers to the terms "orthodromic" and "antidromic." Orthodromic refers to the propagation of an action potential or signal along a nerve fiber in the direction that the action potential or signal normally travels (such as a signal travelling from a peripheral location to a central location in the case of a sensory nerve). In orthodromic monitoring, stimulation to produce a sensory evoked potential is provided distally. The averaging of responses can allow detection of the neural signal amidst noise. Significant prolongation of the latency of the evoked response, or major decline in its amplitude indicates dysfunction of some part of the sensory system. Antidromic refers to the propagation of an action potential or signal along a nerve fiber in the direction opposite to that which the action potential or signal normally travels (in this case, the signal travels from a central location to a peripheral location in a sensory nerve). As used herein, a "nerve" includes branches and tributaries thereof. The disclosure below also refers to the "suitable placement" or "suitable location" with respect to implanting a medical device or performing another procedure on an area of interest of a patient's body. A suitable placement or location is the site of a patient's body where the patient experiences more therapeutic benefit than side effects such that the implantable device, for example, can be ultimately implanted and activated at that site. The disclosure also refers to the term "stimulation." Such a term includes inhibition or activation of electrical activity within a nerve. As used herein with respect to a described element, the terms "a," "an," and "the" include at least one or more of the described element unless otherwise indicated. Further, the term "or" refers to "and/or" unless otherwise indicated.

A brief discussion of the pertinent anatomy and neurophysiology is now provided to assist with understanding the present disclosure. The autonomic nervous system innervates numerous pathways within the human body and consists of two divisions: the sympathetic and the parasympathetic nervous systems. The sympathetic and parasympathetic nervous systems are antagonistic in their action, balancing the other system's effects within the body. The sympathetic nervous system (SNS) usually initiates activity within the body, preparing the body for action, while the parasympathetic nervous system (PNS) primarily counteracts the effects of the SNS.

Figure 1:
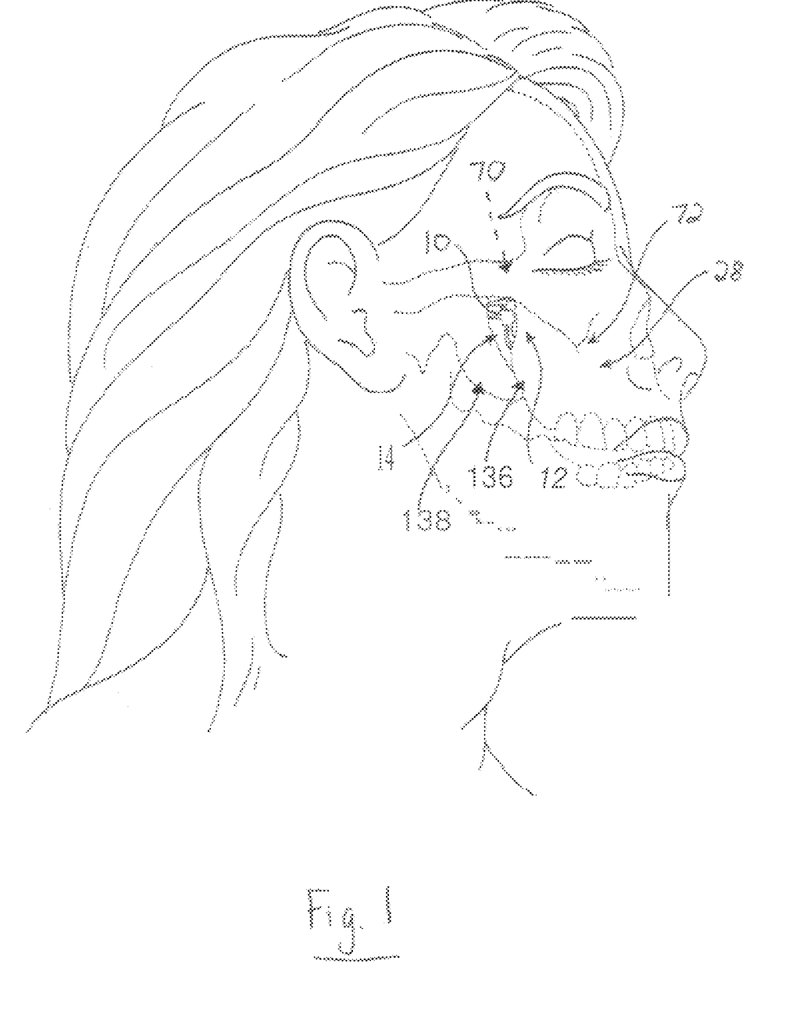
FIG. 1 is a schematic illustration of a human's face and mouth depicting various anatomical structures.

The sphenopalatine ganglia 10 (SPG) are located on both sides of the head (FIG. 1). It shall be assumed for the following description of the present disclosure that reference is being made to the SPG 10 located on the left side of the head. The SPG 10 is located behind the posterior maxilla 12 in the PPF 14, posterior to the middle nasal turbinate (not shown in detail). The SPG 10 is part of the parasympathetic division of the autonomic nervous system; however, the SPG has both sympathetic and parasympathetic nerve fibers, as well as sensory and motor nerve fibers either synapsing within the ganglion (e.g., parasympathetic) or fibers that are passing through the ganglion and not synapsing (e.g., sympathetic, sensory and motor).

The parasympathetic activity of the SPG 10 is mediated through the greater petrosal nerve, while the sympathetic activity of the SPG is mediated through the deep petrosal nerve, which is essentially an extension of the cervical sympathetic chain. Sensory sensations generated by or transmitted through the SPG 10 include, but are not limited to, sensations to the upper teeth, feelings of foreign bodies in the throat, sensations on the lips, gums, nose, cheek, eyelid, eye and persistent itching of the ear. The SPG 10 transmits sensory information, including pain, to the trigeminal system via the maxillary division and ophthalmic division.

The ophthalmic nerve runs along the lateral wall of the cavernous sinus to enter the orbit via the superior orbital fissure. Divisions of this nerve supply sensation to the skin of the nose, eyelids, and forehead including the eye and portions of the nasal mucosa.

The maxillary nerve passes through the inferolateral cavernous sinus and exits the PPF 14. Within the PPF 14, the maxillary nerve gives off several branches including the infraorbital 44, the zygomatic, the nasopalatine 36, the superior alveolar 34, the greater palatine 38, the lesser palatine 40 and the pharyngeal branches.

The infraorbital nerve 44 innervates the lower eyelid, upper lip and part of anterior part of the nasal cavity. The zygomaticotemporal 30 and zygomaticofacial nerves 32 innervate the lateral aspect of the orbit above the zygomatic arch and is distributed to the skin of the side of the forehead.

The nasopalatine 36 enters the nasal cavity through the sphenopalatine foramen, passes across the roof of the nasal cavity below the orifice of the sphenoidal sinus to reach the septum, and then runs obliquely downward and forward between the periosteum and mucous membrane of the lower part of the septum. The nasopalatine nerve 36 descends to the roof of the mouth through the incisive canal and supplies the palatal structure around the upper central and lateral incisors and the canines.

Figure 2:
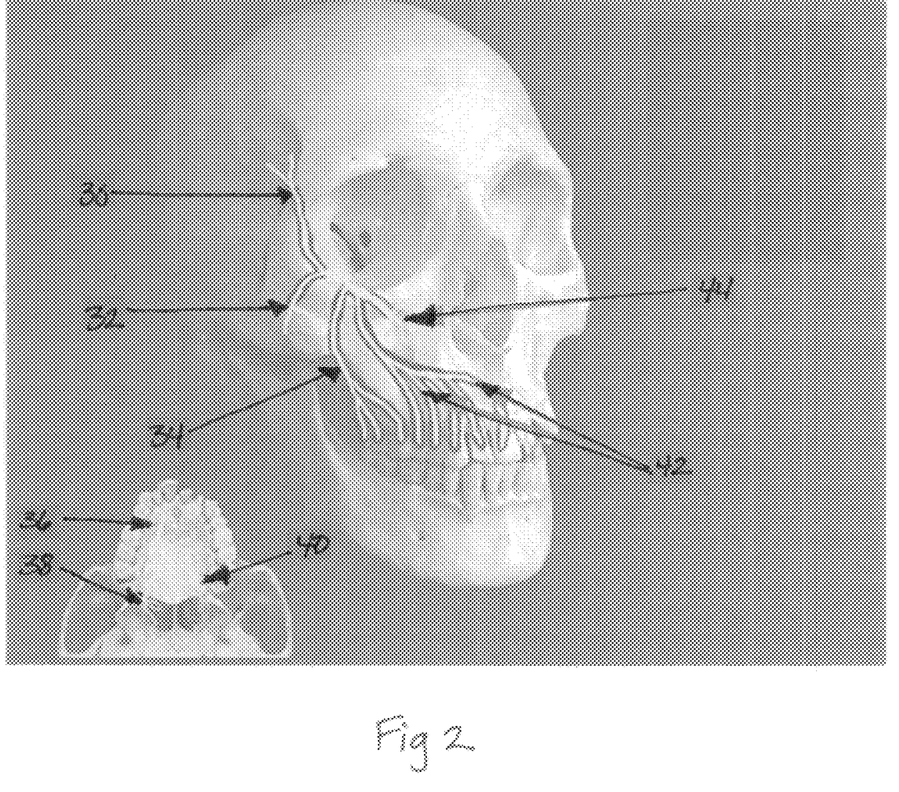
FIG. 2 is a schematic illustration of a skull depicting various anatomic structures.

The posterior superior alveolar branches 34 arise from the trunk of the maxillary nerve just before it enters the infraorbital groove. The posterior superior alveolar branches 34 descend on the tuberosity of the maxilla 136 and give off several branches to the gums and part of the mucous membrane of the cheek. The posterior superior alveolar nerve 34 innervates the second and third maxillary molars, and two of the three roots of the maxillary first molar.

The greater palatine nerve 38 carries both general sensory and parasympathetic fibers. It descends through the greater palatine canal, emerges upon the hard palate through the greater palatine foramen, and passes forward in a groove in the hard palate. It supplies sensation to the gums, the mucous membrane and glands of the hard palate.

The lesser palatine nerve 40 supplies sensation to the soft palate, tonsil and uvula. The pharyngeal nerve is a small branch arising from the posterior part of the PPF 14 and is distributed to the mucous membrane of the nasal part of the pharynx, behind the auditory tube.

The anterior superior alveolar nerve 42 and infraoribtal nerve 44 exit from the infraorbital foramen. The anterior superior alveolar branch 42 descends in a canal in the anterior wall of the maxillary sinus and divides into branches which supply sensation to the incisor and canine teeth. The infraorbital nerve 44 supplies sensation to the lower eyelid, upper lip, and part of the nasal vestibule.

Figure 3:
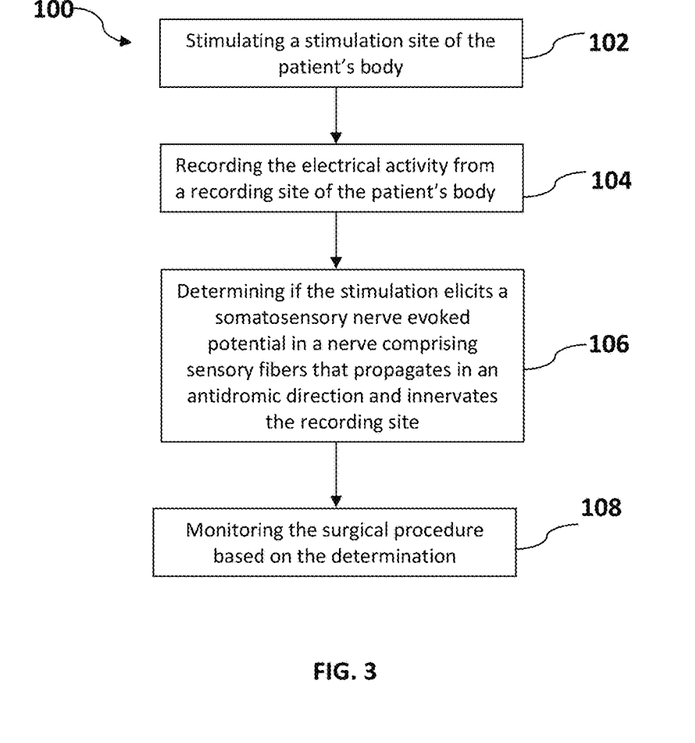
FIG. 3 is flow chart indicating steps of a method of intra-operatively monitoring a surgical procedure according to an embodiment of the present invention.

FIG. 3 describes a method of intra-operatively monitoring a surgical procedure performed on a patient (100). Method 100 comprises stimulating a stimulation site of the patient's body (102) and recording electrical activity from a recording site of the patient's body (104). The stimulating and recording can be done by suitable electrodes known in the art. An exemplary stimulating electrode is described in U.S. patent application Ser. No. 12/765,712 ("the '712 application"), which is incorporated by reference herein. The method further comprises determining if the stimulation elicits a somatosensory nerve evoked potential in a nerve comprising sensory fibers that propagates in an antidromic direction and innervates the recording site (106). The method further includes monitoring the surgical procedure based on the determination (108). Because such a method involves antidromic monitoring, the recording site of the somatosensory nerve evoked potential is distal to the stimulation site.

In certain embodiments, the stimulation site is part of the patient's autonomic nervous system. In a preferred embodiment, the stimulation site is within the PPF. In a more preferred embodiment, the stimulation site is the SPG. In such embodiments, the recording site is a site on the patient's face, nasal cavity and/or mouth. According to an exemplary method, the surgical procedure is implanting a neurostimulator in a patient's body at a suitable implantation site, such as within the PPF. The neurosurgical procedure is monitored to identify the suitable implantation site by navigating a surgical pathway to the suitable implantation site. For example, according to a method, the SPG is electrically stimulated and electrical activity is recorded at a recordation site distal to the SPG to see if sensory nerves innervating the recordation site are also being stimulated while the SPG is being stimulated.

There are numerous sensory nerves located near the SPG and SPG stimulation can create an electrical field that also inadvertently stimulates some of these sensory nerves that innervate various areas of the patient's body. A clinician wants to minimize activation of these nerves during SPG stimulation because such activation can cause pain or discomfort in various areas innervated by those sensory nerves. Such nerves can include trigeminal nerve branches that supply various regions of a patient's mouth and face. Non-limiting examples of sensory nerves include the superior labial nerve, the greater palatine nerve, the lesser palatine nerve, the superior posterior alveolar nerve, the zygomaticotemporal nerve, the nasopalatine nerve, the superior gingival branches, superior dental plexus, nasal branch of infraorbital nerve, anterior superior alveolar nerve, and inferior palpebral branches. One or more of these nerves innervate various areas of a patient's face and mouth and can be the recordation site for recording somatosensory nerve evoked potentials. These areas include, for example, the patient's upper lip, hard palate, soft palate, upper gum, gingival, infraorbital rim, nasal cavity, external naris, nasopharygnx, cheek, eyelid, eye, or any suitable combination thereof. Normally, these various areas have sensory nerves that are activated when pain, temperature, pressure, or touch occurs and these nerves send a signal in the orthodromic direction to the pain center in the brain. In the above-described exemplary method, the SPG is stimulated and a clinician can observe whether a particular area of the patient's face or mouth (i.e. the recordation site) receives a signal from a sensory nerve that is inadvertently stimulated while the SPG is stimulated and thus sends a signal antidromically back to the particular area of the patient's face or mouth. In such a method, a clinician taps into a sensory nerve at some point along its path from the periphery to a central target, potentially stimulates the nerve, and observes whether any somatosensory nerve evoked potential is detected at a peripheral recording site innervated by the nerve (such as on the patient's face, nasal cavity or mouth). If a nerve evoked potential is detected at a recording site, then the clinician is informed that leaving the stimulation electrode at the existing stimulation site with the existing stimulation parameters will result in unwanted stimulation of sensory nerves innervating the recording site. As such, signals will be transmitted by the sensory nerves to the same central location that is responsible for pain perception and the clinician will know that if he continues the existing stimulation, the patient may perceive pain at the recordation site. The clinician can then either move the stimulating electrode or change the stimulation parameters, for example, to produce an electrical field that will stimulate the SPG but avoid recruiting the sensory nerve that is responsible for pain at the recordation site.

Thus, an advantage of antidromic monitoring is that a clinician can identify locations within the PPF, near the SPG, to perform stimulation to clinically block or activate the SPG, but also avoid activating trigeminal nerve branches that innervate the upper teeth, for example. Activation of these nerves can cause patient discomfort, thus effectively limiting the stimulation field strength that is used to stimulate the SPG. In addition to avoiding such nerves that innervate the teeth, for example, trial stimulation of the SPG can be monitored to determine its effectiveness by observing stimulating induced autonomic systems. Such systems are a reliable surrogate for suitable neurostimulator placement and successful therapeutic outcomes. Therefore, the desired neurostimulator location is one that is placed near the SPG but not near the sensory nerve fibers innervating the teeth, for example. In other words, the presence of cranial autonomic symptoms and the absence of activation of nerves innervating the teeth, for example, upon SPG stimulation can be used to determine a suitable neurostimulator placement. If these properties are not achieved, the clinician would know that the neurostimulator placement is not suitable and could re-position the neurostimulator and repeat the stimulation and recording steps as described above until a suitable implantation location is determined.

Antidromic somatosensory evoked potentials are single event physiological responses, in which the clinician accesses the same nerve fibers with both the stimulating and recording electrodes rather than having to rely on recording cortical signals commonly used in orthodromic monitoring. In antidromic monitoring as described herein, the stimulation is proximal to the region at risk thus causing a robust backward, or antidromic, physiological response that is recorded distally. This large potential is easily obtained without need for signal averaging and therefore allows for substantially real time feedback from recording electrodes. As such, the nerve evoked potentials can be observed in substantially real time with the nerve evoked potentials being capable of being detected within seconds after the stimulation site is stimulated as opposed to within minutes after stimulation.

Figure 4:
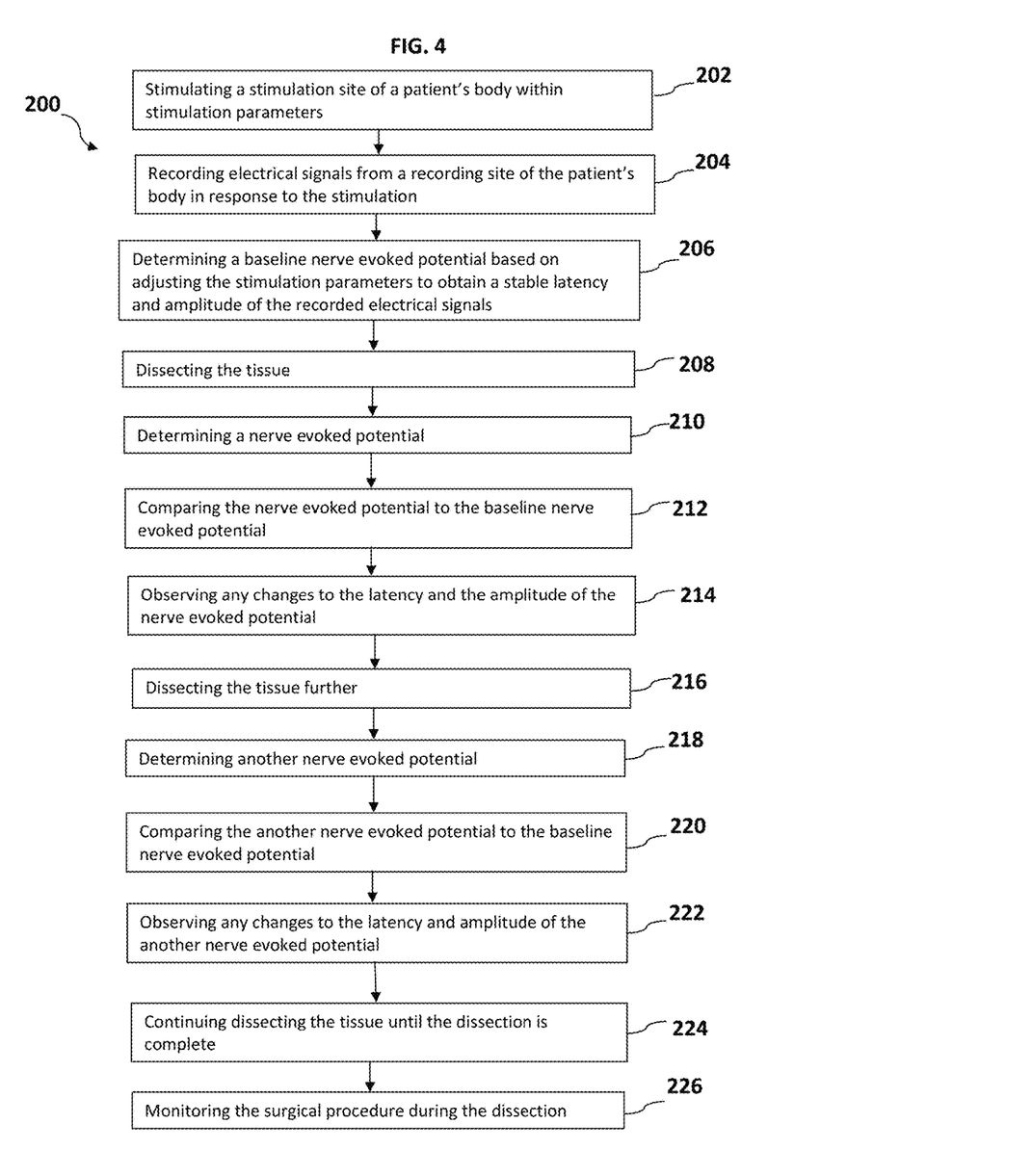
FIG. 4 is flow chart indicating steps of a method of intra-operatively monitoring a surgical procedure according to another embodiment of the present invention.

Referring to FIG. 4, an embodiment of a method of intra-operatively monitoring a surgical procedure involving tissue dissection of a patient's body (200) is provided. An exemplary method will be described with respect to placing a neurostimulator within the PPF, such as at the SPG, but it is understood that this method can apply to other procedures involving dissection of a patient's tissue. This method comprises stimulating a stimulation site of a patient's body within stimulation parameters (202). A subdermal stimulating electrode can be placed at the stimulation site to provide the stimulation. The stimulating electrode can be, for example, about 7.0 millimeters (mm) in height and about 0.4 mm in diameters. The stimulating electrode can be placed, for example, about 1.0 centimeters (cm) apart for multiple stimulation sites. An exemplary stimulating electrode is described in the '712 application, which is incorporated by reference herein. The stimulation site is stimulated continuously within stimulation parameters during the dissection process. Exemplary stimulation parameters are a pulse duration of about 200 microseconds, a repetition rate of about 2.7 to about 4.8 seconds (depending on the noise and signal quality of the electrical signals), an impedance of about 0.5 to about 5 kOhms, and a stimulation intensity of about 5 to about 10 mA.

The method also includes recording electrical signals from a recording site of a patient's body in response to the stimulation (204). Recording electrodes can be, for example, about 13.0 mm in height and about 0.4 mm in diameter. A grounding electrode can be placed on the shoulder, for example.

The method further comprises determining a baseline nerve evoked potential based on adjusting the stimulation parameters to obtain a stable latency and amplitude of the recorded electrical signals (206). For example, the intraoperative team can adjust the stimulation parameters if the electrical signals are absent or suboptimal in order to maximize the baseline electrical signals. Following stability of the electrical signals in latency and amplitude, the latency and amplitude of the electrical signals can be averaged (in the case of orthodromic monitoring, for example, as described below) and these averaged electrical signals are referenced as the baseline nerve evoked potential. The baseline nerve evoked potential can be an averaged response of about, for example 150 to about 300 stimulation events. The baseline nerve evoked potential can be used to determine a warning criteria to a clinician if changes, for example, are greater than about a 10% increase in latency or less than about a 50% decrease in amplitude.

Surgical dissection then begins and the patient's tissue is dissected (208). For example, in the case of placing a neurostimulator within the PPF, gingival buccal incision is done and the clinician can perform an approximate 1 to 1.5 cm initial dissection, such as a 1.0 cm dissection, and then remove the dissection device. The nerve evoked potential then can be determined (210) and compared to the baseline nerve evoked potential (212). Any change to the latency and the amplitude of the nerve evoked potential is observed (214). For example, if the nerve evoked potential is different from the baseline nerve evoked potential, the clinician can reduce the amount of force applied to the tissue and/or manipulate the surgical pathway to avoid any further insult to the patient's neural tissue.

The surgical procedure continues and the tissue is dissected further (216). For example, the tissue can be dissected further another approximate 1 to 1.5 cm, such as a 1.0 cm dissection, and another nerve evoked potential is determined (218). The another nerve evoked potential is compared to the baseline nerve evoked potential (220) and any change to the latency and amplitude of the another nerve evoked potential is observed (222). The method further comprises continuing to dissect the tissue until the dissection is complete (224). Steps (208) to (222) may take between about 5 to about 15 minutes. The surgical procedure is monitored during the dissection process (226).

As stated above, in certain embodiments, the surgical procedure is implanting a neurostimulator in a patient's body such as, for example, in the PPF, and more specifically on the SPG. The surgical procedure can be monitored to identify a suitable location for the neurostimulator, evaluate the function of nerves during the procedure, and/or determine if any damage to neural structures or other unintended tissue damage occurs during the procedure. In the case of implanting a neurostimulator within the PPF, such a process can minimize damage to the trigeminal nerve during the dissection process to allow for suitable placement of a neurostimulator within the PPF.

As indicated above, in certain embodiments, the nerve evoked potential is an orthodromic nerve evoked potential. In such an embodiment, the electrical signals are averaged to determine a baseline nerve evoked potential. Further, in orthodromic monitoring, the stimulation site is innervated by a peripheral nerve that receives electrical input from the recording site. The peripheral nerve can be a cranial nerve, a spinal nerve a sensory nerve or any combination thereof. A non-limiting example of a cranial nerve is the trigeminal nerve. The stimulation site can be innervated by a superior labial nerve, a greater palatine nerve, a lesser palatine nerve, a superior alveolar nerve, a zygomaticotemporal nerve, a nasopalatine nerve, a superior gingival branch, a superior dental plexus, a nasal branch of an infraorbital nerve, an anterior superior alveolar nerve, an inferior palpebral branch, or and any suitable combinations thereof.

The stimulation site can be the patient's upper lip, hard palate, soft palate, upper gum, gingival, infraorbital rim, nasal cavity, external naris, nasopharygnx, cheek, eyelid, eye, or any suitable combination thereof. The recording site can be the scalp. For example, the recording site can be CP5, CP6, CPz or Fz (based on the International 10-20 system for location of scalp electrodes). The recording site can also be the left mastoid process, the right mastoid process or any suitable combination of the above recording sites.

In other embodiments, the nerve evoked potential is an antidromic nerve evoked potential. In such an embodiment, the recording site is innervated by a peripheral nerve that receives electrical input from the stimulation site. The peripheral nerve can be a cranial nerve, a spinal nerve, a sensory nerve or any suitable combination thereof. An exemplary cranial nerve is the trigeminal nerve. The recording site can be innervated by a superior labial nerve, a greater palatine nerve, a lesser palatine nerve, a superior alveolar nerve, a zygomaticotemporal nerve, a nasopalatine nerve, a superior gingival branch, a superior dental plexus, a nasal branch of an infraorbital nerve, an anterior superior alveolar nerve, an inferior palpebral branch, or any suitable combinations thereof. The recording site can be the patient's upper lip, hard palate, soft palate, upper gum, gingival, infraorbital rim, nasal cavity, external naris, nasopharygnx, cheek, eyelid, eye, or any suitable combination thereof. The stimulation site can be the scalp, inside the pterygopalatine fossa (such as, for example, the SPG), or any suitable combination thereof. In the case of the scalp, the stimulation site can be the CP5, CP6, CPz or Fz (based on the International 10-20 system for location of scalp electrodes). The stimulation site can also be the left mastoid process, the right mastoid process or any suitable combination of the above stimulation sites for antidromic monitoring. In cases where the stimulation site and the recording site are in close proximity as described above, the antidromic monitoring can provide a substantially real-time indication of the nerve evoked potentials.

In the case of placing a neurostimulator in the PPF, the neurostimulator, such as that described in the '712 application (incorporated by reference herein) can be configured for implantation in the PPF 14. Other neurostimulators can also be used. A neurostimulator can generally include any active implantable medical device configured to deliver electrical stimulation, alone or in combination with other types of stimulation to tissue of a subject. The neurostimulator (not shown) can further include any active implantable medical device configured for implantation for a relatively short period of time (e.g., to address acute medical conditions) or a relatively long period of time (e.g., to address chronic medical conditions). Additionally, the neurostimulator can include one or more elements used to record or monitor a physiological response of a subject's tissue (e.g., a delivered therapy), as well as one or more other components that interface with the patient's tissue (e.g., therapeutic agent delivery mechanisms, sensors, etc.).

In an example, a neurostimulator can be implanted as disclosed in the '712 application, i.e., such that the stimulator body is positioned sub-periosteally medial to the zygoma 70 (FIG. 1) on the posterior maxilla 12 within the buccal fat pad (not shown) of the cheek, and the integral fixation apparatus is anchored to the zygomaticomaxillary buttress 72 (FIG. 1) such that the integral stimulation lead is placed within the PPF 14 (FIG. 1) or, more specifically, in close proximity (e.g., about 1-5 mm) to the SPG 10.

The surgical procedure that is monitored can be a wide variety of procedures where monitoring SSEPs is a useful indicator of the course, success, or progress of the procedure. For example, the neurosurgical procedure can be stimulating the SPG with an implantable neurostimulator lead comprising an electrode. Such a procedure can be used to treat different medical conditions, such as headaches and other disorders as disclosed in U.S. application Ser. No. 13/470,480, filed on May 14, 2012 and Ser. No. 13/476,224, filed on May 21, 2012, both of which are incorporated by reference.

Monitoring the surgical procedure can include monitoring an array of factors that contribute to the success of the procedure. Such factors include, but are not limited to, surgical navigation, prevention of iatrogenic injury and target ablation. For example, the surgical procedure can be monitored using the recorded SSEPs to determine the optimal location of a neurostimulator lead or other medical device in the patient's body. In the case of stimulating the SPG, recorded SSEPs can be used to help optimize the placement of an implantable neurostimulator lead inside the PPF, near the SPG. Monitoring can also include determining if any damage to neural structures occurs during the procedure, such as damage to the trigeminal nerve branches, or if there is the potential for damage to neural structures such that the procedure can be modified to minimize such risk.

The foregoing description and examples have been set forth merely to illustrate the invention and are not intended as being limiting. Each of the disclosed aspects and embodiments of the present invention may be considered individually or in combination with other aspects, embodiments, and variations of the invention. Further, while certain features of embodiments of the present invention may be shown in only certain figures, such features can be incorporated into other embodiments shown in other figures while remaining within the scope of the present invention. In addition, unless otherwise specified, none of the steps of the methods of the present invention are confined to any particular order of performance. Modifications of the disclosed embodiments incorporating the spirit and substance of the invention may occur to persons skilled in the art and such modifications are within the scope of the present invention. Furthermore, all references cited herein are incorporated by reference in their entirety.

What is claimed is:

1. A method of implanting a neurostimulator in a patient's body comprising:

stimulating a stimulation site of the patient's body with an electrode having stimulation parameters;

obtaining a measurement of a somatosensory nerve evoked potential (SSEP) to determine whether the stimulation of the stimulation site elicits a SSEP in a nerve comprising sensory fibers that are responsible for the patient's perception of pain or discomfort at a recording site, the nerve propagating in an antidromic direction and innervating the recording site, the recording site located on the face, nasal cavity or mouth of the patient's body;

minimizing stimulation of the sensory fibers such that the patient's perception of pain or discomfort at the recording site is minimized by adjusting the stimulation parameters and/or the electrode position in response to the stimulation of the stimulation site eliciting SSEP;

determining an implantation site for the neurostimulator as suitable based on the minimizing and the measurement;

navigating a surgical pathway to the suitable implantation site; and implanting the neurostimulator in the patient's body at the suitable implantation site.

2. The method of claim 1, wherein stimulating the stimulation site of the patient's body comprises stimulating a stimulation site of the patient's autonomic nervous system.

3. The method of claim 2, wherein the stimulation site is a sphenopalatine ganglion (SPG).

4. The method of claim 1, wherein the suitable implantation site is within a pterygopalatine fossa (PPF).

5. The method of claim 1, wherein the nerve is at least one of a superior labial nerve, a greater palatine nerve, a lesser palatine nerve, a posterior superior alveolar nerve, a zygomaticotemporal nerve, a nasopalatine nerve, a superior gingival branch, a superior dental plexus, a nasal branch of an infraorbital nerve, an anterior superior alveolar nerve, or an inferior palpebral branch.

6. The method of claim 1, wherein the suitable implantation site is within the skull of the patient.

7. The method of claim 1, wherein the suitable implantation site is within the maxillofacial region of the patient.

8. The method of claim 1, wherein the somatosensory nerve evoked potential is measured in substantially real-time.

* * * * *